United States Patent [19] [11] 4,259,322
Lim [45] Mar. 31, 1981

[54] METHOD OF TREATMENT OF TUBERCULOSIS

[76] Inventor: Helong Lim, 662 Union St., Vancouver, British Columbia, Canada, V6A 2B9

[21] Appl. No.: 887,996

[22] Filed: Mar. 20, 1978

[51] Int. Cl.³ .............................................. A61K 33/18
[52] U.S. Cl. ..................................................... 424/150
[58] Field of Search ......................................... 424/150

[56] References Cited

PUBLICATIONS

Chemical Abstracts 34: 6367 (6) (1940).
Conn, Current Therapy 1977, 1977 pp. 151–156.

*Primary Examiner*—Jerome D. Goldberg
*Attorney, Agent, or Firm*—Howard I. Podell

[57] ABSTRACT

A tuberculosis medication using approximately 10 grams of calcium gluconate combined with approximately 4 grams of sodium iodine in a vehicle of water to a volume of 100 ccs can be used for intramuscular or intravenous injections at a rate of 5 or 10 ccs per injection to relieve and treat tuberculosis.

3 Claims, 1 Drawing Figure

METHOD OF TREATMENT OF TUBERCULOSIS

BACKGROUND OF THE INVENTION

I have invented a new and novel tuberculosis medication. My improved medication can treat tuberculosis of the pulmonary system glandular system bones and the intestines. Further, this improved medication is of particular value in its ability to kill the tubercle baccillus directly and to dissolve caseation of the focus, thereby producing a radical treatment with no side effects in the patients. The medication has been used at various treatment rates and at various times during research done over several years and has established a successful cure record.

Prior art references known at the time of preparation of this application include the following U.S. Pat. Nos. 1,903,614, 1,889,195, 1,435,335, 87,603, 308,596, and 112,329.

BRIEF DESCRIPTION OF THE INVENTION

My improved tuberculosis medication utilizes a portion of calcium gluconate combined with a portion of sodium iodine by mixing to which distilled water is added to form a product a portion of which is used for the individual treatments by injection either intravenously or intramuscularly.

BRIEF DESCRIPTION OF THE FIGURES

My invention can be understood in view of the accompanying figure.

DETAILED DESCRIPTION OF THE PREFERRED EMBODIMENT

Figure 1:
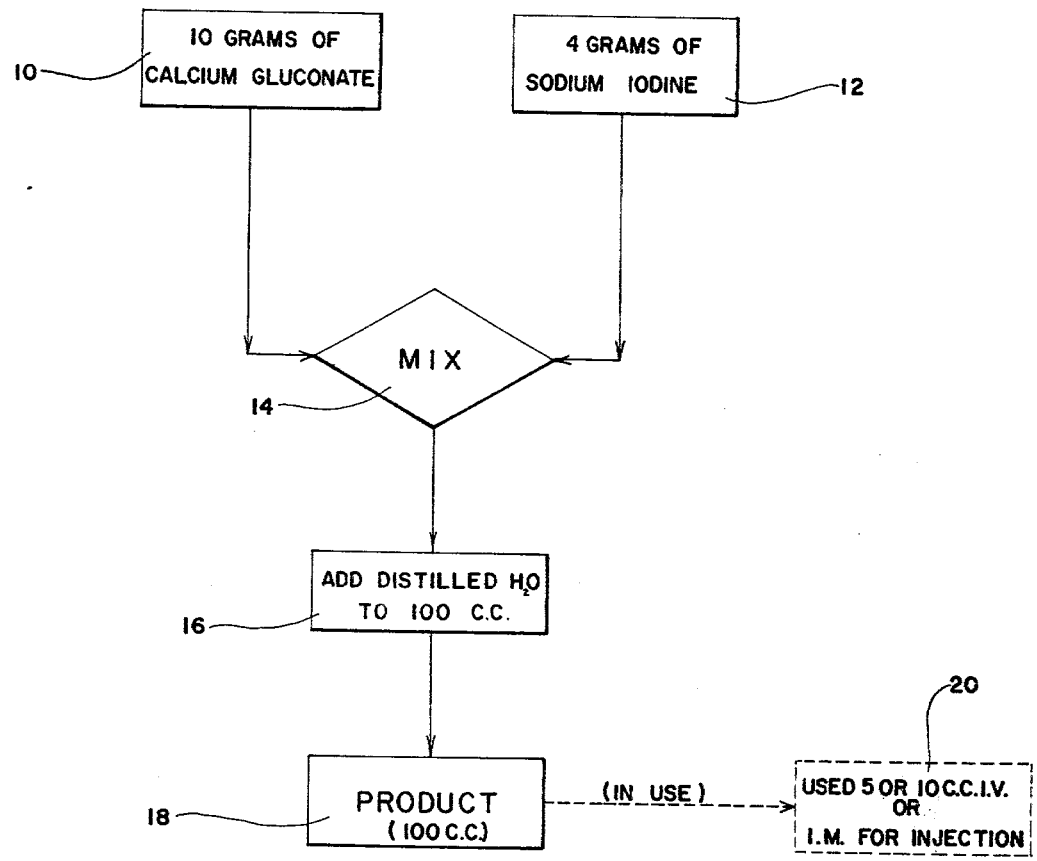
FIG. 1 is a schematic diagram showing the preparation and use of the medication formulation.

With regard to FIG. 1, 10 grams of calcium gluconate 10 can be combined with 4 grams of sodium iodine 12 by mixing 14 and distilled water 16 can be added to the mixture 14 to a volumn of 100 ccs 16 in order to produce a product 18 which can be used 20 in 5 or 10 cc intravenous or intramuscular injections 20 for treatment of the individual patient.

Having described a preferred embodiment of my invention, it is understood that various changes can be made without departing from the spirit of my invention, and, I desire to cover by the appended claims all such modifications as fall within the true spirit and scope of my invention.

What I claim and seek to secure by Letters Patent is:

1. A method for treating tuberculosis in a patient comprising administering to a patient having tuberculosis, by injection to the patient, an effective amount of killing tubercle bacillus medication of the following composition:
   an aqueous solution of the ingredients of
   calcium gluconate and sodium iodine, in which
   the proportions by weight of the said ingredients in a said aqueous solution of approximately 100 cc. comprise
   a quantity of calcium gluconate of approximately 10 grams and
   a quantity of sodium iodine of approximately 4 grams.
2. The method recited in claim 1 in which the portion of the medication is administered by an intravenous injection to the patient.
3. The method recited in claim 1 in which a portion of the medication is administered by an intramuscular injection to the patient.

* * * * *